US011317879B2

(12) United States Patent
Lee et al.

(10) Patent No.: US 11,317,879 B2
(45) Date of Patent: May 3, 2022

(54) APPARATUS AND METHOD FOR TRACKING LOCATION OF SURGICAL TOOLS IN THREE DIMENSION SPACE BASED ON TWO-DIMENSIONAL IMAGE

(71) Applicant: KOREA INSTITUTE OF SCIENCE AND TECHNOLOGY, Seoul (KR)

(72) Inventors: Deukhee Lee, Seoul (KR); Sangchul Hwang, Seoul (KR); Sung Chul Kang, Seoul (KR); Youngjun Kim, Seoul (KR); Se Hyung Park, Seoul (KR)

(73) Assignee: Korea Institute of Science and Technology, Seoul (KR)

(*) Notice: Subject to any disclaimer, the term of this patent is extended or adjusted under 35 U.S.C. 154(b) by 435 days.

(21) Appl. No.: 15/631,032

(22) Filed: Jun. 23, 2017

(65) Prior Publication Data

US 2018/0249973 A1 Sep. 6, 2018

(30) Foreign Application Priority Data

Mar. 6, 2017 (KR) ........................ 10-2017-0028217

(51) Int. Cl.
*A61B 6/12* (2006.01)
*A61B 34/20* (2016.01)
(Continued)

(52) U.S. Cl.
CPC ................ *A61B 6/12* (2013.01); *A61B 34/20* (2016.02); *A61B 90/361* (2016.02);
(Continued)

(58) Field of Classification Search
CPC ...... A61B 2034/102; A61B 2034/2057; A61B 34/20; A61B 6/12; A61B 2090/3966;
(Continued)

(56) References Cited

U.S. PATENT DOCUMENTS

| | | | |
|---|---|---|---|
| 7,756,244 | B2 | 7/2010 | Mostafavi |
| 8,428,690 | B2 | 4/2013 | Li et al. |

(Continued)

FOREIGN PATENT DOCUMENTS

| | | |
|---|---|---|
| JP | 2002-204832 A | 7/2002 |
| JP | 2009-000389 A | 1/2009 |

(Continued)

OTHER PUBLICATIONS

Christophe Doignon, "An Introduction to Model-Based Pose Estimation and 3-D Tracking Techniques", Scene Reconstruction, Pose Estimation and Tracking, Jun. 2007, pp. 359-382.

(Continued)

*Primary Examiner* — Boniface Ngathi N
*Assistant Examiner* — Milton Truong
(74) *Attorney, Agent, or Firm* — Rabin & Berdo, P.C.

(57) ABSTRACT

Embodiments relate to a method for tracking a location of a surgical tool based on a radiographic image, which includes: by a photography system, photographing a surgical tool having a physical marker frame composed of three or more marker bands; by an information processor, detecting a center point of each marker band in the photographed image; and by the information processor, estimating a three-dimensional location of the surgical tool based on a distance between the detected center point and a center point of a true marker band, and a tracking apparatus for the same.

12 Claims, 20 Drawing Sheets

X-ray source
$l_1$ $l_2$ $l_3$
$c_1(p_1, p_2, p_3)$ $c_2$ $c_3$
$\delta_1$ $\delta_2$
$x_0$ $(\mu_0, v_0)$
$x_1$ $(\mu_1, v_1)$
$x_2$ $(\mu_2, v_2)$
50
Projection plane

(51) Int. Cl.

| | |
|---|---|
| ***A61B 90/00*** | (2016.01) |
| *A61M 25/01* | (2006.01) |
| *A61M 25/00* | (2006.01) |
| *A61B 34/10* | (2016.01) |
| *A61B 6/00* | (2006.01) |

(52) U.S. Cl.

CPC ....... *A61B 6/5294* (2013.01); *A61B 2034/102* (2016.02); *A61B 2034/2057* (2016.02); *A61B 2034/2065* (2016.02); *A61B 2090/365* (2016.02); *A61B 2090/367* (2016.02); *A61B 2090/3937* (2016.02); *A61B 2090/3966* (2016.02); *A61M 25/0108* (2013.01); *A61M 2025/0008* (2013.01)

(58) Field of Classification Search

CPC .......... A61B 2090/3937; A61B 90/361; A61B 2090/367; A61M 2025/0008; A61M 25/0108

See application file for complete search history.

(56) References Cited

U.S. PATENT DOCUMENTS

| | | | | |
|---|---|---|---|---|
| 8,682,062 | B2 | 3/2014 | Kim et al. | |
| 2003/0181809 | A1* | 9/2003 | Hall | A61B 6/12 600/425 |
| 2009/0226063 | A1* | 9/2009 | Rangwala | G06T 7/0012 382/128 |
| 2009/0312629 | A1* | 12/2009 | Razzaque | A61B 5/06 600/426 |
| 2012/0071751 | A1* | 3/2012 | Sra | A61B 6/12 600/424 |
| 2012/0082342 | A1* | 4/2012 | Kim | G06T 7/74 382/103 |
| 2012/0289825 | A1* | 11/2012 | Rai | A61B 6/12 600/425 |
| 2013/0243153 | A1* | 9/2013 | Sra | A61B 6/022 378/41 |
| 2014/0018788 | A1* | 1/2014 | Engelman | A61B 18/18 606/33 |
| 2014/0058251 | A1* | 2/2014 | Stigall | A61B 5/1076 600/424 |
| 2014/0321710 | A1* | 10/2014 | Robert | A61B 6/12 382/103 |
| 2015/0087881 | A1* | 3/2015 | Miyamoto | A61B 6/5211 600/1 |

FOREIGN PATENT DOCUMENTS

| | | | |
|---|---|---|---|
| KR | 10-0640761 | B1 | 11/2006 |
| KR | 10-1188715 | B | 10/2012 |
| KR | 10-2014-0065541 | A | 5/2014 |
| KR | 10-1449830 | B | 10/2014 |
| KR | 10-1652888 | B | 9/2016 |
| WO | WO 2006/124388 | A1 | 11/2006 |
| WO | WO 2013/036831 | A1 | 3/2013 |

OTHER PUBLICATIONS

Christophe Doignon et al., "Pose estimation and feature tracking for robot assisted surgery with medical imaging", Unifying Perspectives in Computational and Robot Vision, 2008, vol. 8, pp. 79-101.

* cited by examiner

FIG. 7C

| Center position of the markers | | | |
|---|---|---|---|
| the true position | | Estimated position | |
| x | y | x | y |
| 512 | 784.2955 | 512.8984 | 784.9339 |
| 512 | 751.3289 | 512.9014 | 751.6966 |
| 512 | 718.4402 | 512.8988 | 718.7591 |

Resampled pmb

FIG. 18

| No. | Point1[mm] | point2[mm] | point3[mm] | point4[mm] | point5[mm] | point6[mm] |
|---|---|---|---|---|---|---|
| 1 | 1.601005 | 1.654448 | 1.707981 | 0.429486 | 0.437685 | 0.445904 |
| 2 | 0.386802 | 0.507921 | 0.632179 | 0.105601 | 0.143711 | 0.192581 |
| 3 | 0.159026 | 0.218722 | 0.280469 | 0.095728 | 0.095426 | 0.102064 |
| 4 | 0.147167 | 0.147167 | 0.147167 | 0.655442 | 0.603865 | 0.552435 |
| 5 | 0.465053 | 0.467483 | 0.469915 | 0.11113 | 0.433498 | 0.802991 |
| 6 | 0.918399 | 0.89221 | 0.866136 | 1.867488 | 1.612531 | 1.357667 |
| 7 | 0.612824 | 0.624694 | 0.636567 | 2.033922 | 1.850851 | 1.667821 |
| Avg. | 0.612897 | 0.644664 | 0.677202 | 0.756971 | 0.739652 | 0.731638 |

APPARATUS AND METHOD FOR TRACKING LOCATION OF SURGICAL TOOLS IN THREE DIMENSION SPACE BASED ON TWO-DIMENSIONAL IMAGE

CROSS-REFERENCE TO RELATED APPLICATION

This application claims priority to Korean Patent Application No. 10-2017-0028217, filed on Mar. 6, 2017, and all the benefits accruing therefrom under 35 U.S.C. § 119, the contents of which in its entirety are herein incorporated by reference.

BACKGROUND

1. Field

The present disclosure relates to an apparatus and method for tracking a location of a surgical tool, and more particularly, to an apparatus and method for tracking a three-dimensional location of a surgical tool based on a location of a marker attached to the surgical tool in a two-dimensional image. In particular, the present disclosure relates to estimating location and shape information of a catheter from a single X-ray image (not several X-ray images) obtained by attaching a marker band to the catheter and photographing the marker band during the epidural endoscopy.

Description About National Research and Development Support

This study was supported by Project No. 1415143890 of Korea Institute for Advancement of Technology and Project No. 10052980 of Korea Evaluation Institute of Industrial Technology.

2. Description of the Related Art

In these days, back diseases are frequently found at not only old persons but also young persons. Among back diseases, herniation of intervertebral disc, which is known as so-called "disc", demands surgical operations when it is severe.

Such a surgical operation may give a serious burden on a patient due to a large incision. Thus, in these days, non-invasive epidural epiduroscopy is more frequently performed. However, in the epidural epiduroscopy, a catheter is inserted into a diseased area by utilizing anatomical knowledge obtained from medical images before the surgical operation and also two-dimensional X-ray images taken during the surgical operation, and thus surrounding tissues such as main blood vessels, nerves and fasciae may be damaged when the catheter is inserted.

In addition, in order to accurately insert the catheter, X-ray images are taken in several directions during the surgical operation, and thus it is inevitable that both a patient and a doctor are exposed to X rays for a long time.

To solve this problem, a three-dimensional location tracking technique has been introduced to a surgical instrument by applying a computer vision technology, and Non-patent Literatures 1 and 2 below propose an algorithm for estimating a three-dimensional posture of a surgical instrument by using markers of a measurer on the same line. However, the proposed method is applied to a rigid endoscope, and the rigid endoscope is not applied to various surgical operations since its front end has a limited operating angle.

RELATED LITERATURES

Patent Literature (Patent Literature 1) Korean Patent Registration No. 10-1449830

(Patent Literature 2) Korean Patent Registration No. 10-1188715

Non-Patent Literature (Non-patent Literature 1) C. Doignon, "An Introduction to Model-Based Pose Estimation and 3D Tracking Techniques," Scene Reconstruction, Pose Estimation and Tracking, pp. 359-382, 2007.

(Non-patent Literature 2) C. Doignon, F. Nageotte, B. Maurin and A. Krupa, "Pose estimation and feature tracking for robot assisted surgery with medical imaging," Unifying Perspectives in Computational and Robot Vision, Vol. 8, pp. 79-101, 2008.

SUMMARY

In order to solve the above problems, embodiments of the present disclosure propose an apparatus and method for estimating a three-dimensional location of a surgical tool from a photographed image in a state where a surgical tool having a front end whose operating angle is freely adjustable is inserted into a surgical site. In more detail, embodiments of the present disclosure propose an apparatus and method for determining a reference point (for example, a center point of a marker band) of a surgical tool in a photographed image.

In one aspect of the present disclosure, there is provided an apparatus for tracking a location of a surgical tool based on a radiographic image, comprising: a photography system configured to photograph a surgical tool having a physical marker frame; and an information processor configured to estimate a three-dimensional location of the surgical tool based on the physical marker frame in the photographed image, wherein the physical marker frame includes three or more marker bands which surrounds a part of the surgical tool.

In an embodiment, the information processor may detect a center point of each marker band in the image, and the information processor may estimate a three-dimensional location of the surgical tool based on a distance between the detected center point in the image and a center point of a true marker band.

In an embodiment, the surgical tool may include two or more physical marker frames, and the two or more physical marker frames may have axes different from each other.

In an embodiment, an interval between the marker bands may be greater than 1.5 times of a width of each marker band.

In an embodiment, the photography system may be a radiography system, and the marker bands may be made of a conductor, and a non-conductor may be provided between the marker bands.

In an embodiment, the radiography system may be an X-ray photography system.

In an embodiment, the surgical tool may be a bendable catheter.

In an embodiment, the surgical tool may be further included.

In an embodiment, the information processor may generate a surgical tool model corresponding to the surgical tool on a three-dimensional virtual space, based on the estimated three-dimensional location of the surgical tool, and the information processor may display the generated surgical tool model on a display together with the image.

In an embodiment, the information processor may resample the photographed image and determine a center point of each marker band in the resampled image.

In an embodiment, the information processor may generate a virtual marker frame corresponding to the physical marker frame on a three-dimensional virtual space, project the generated virtual marker frame to the photographed image, adjust a location of the virtual marker frame on the three-dimensional space so that the virtual marker frame projected to the image is matched with the physical marker frame, and when the projected virtual marker frame is matched with the physical marker frame, determine a center point of the marker band of the virtual marker frame in the image as a center point of the marker band of the physical marker frame.

In an embodiment, the information processor may adjust the location of the virtual marker frame along a line connecting the photography system and the physical marker frame, on the three-dimensional virtual space.

In another aspect of the present disclosure, there is provided a method for tracking a location of a surgical tool based on a radiographic image, comprising: by a photography system, photographing a surgical tool having a physical marker frame composed of three or more marker bands; by an information processor, detecting a center point of each marker band in the photographed image; and by the information processor, estimating a three-dimensional location of the surgical tool based on a distance between the detected center point and a center point of a true marker band.

In another aspect of the present disclosure, there is provided a method for tracking a location of a surgical tool based on a radiographic image, comprising: by a photography system, photographing a surgical tool having a physical marker frame composed of three or more marker bands; by an information processor, detecting a center point of each marker band in the photographed image; by the information processor, estimating a three-dimensional location of the surgical tool based on a distance between the detected center point in the image and a center point of a true marker band; and correcting a three-dimensional location by using a contour of the surgical tool in the image.

According to an embodiment of the present disclosure, the amount of exposed X rays may be reduced in comparison to the existing case since a three-dimensional location of a surgical tool is tracked using a single X-ray image photographed during a surgical operation. In addition, by using the three-dimensional shape information of the inserted surgical tool, it is possible to improve less invasiveness, accuracy and dexterity.

BRIEF DESCRIPTION OF THE DRAWINGS

FIGS. 7A to 7C show experimental examples for illustrating a case where an error is generated between a true marker frame and a three-dimensional location of a marker frame estimated based on a center point of the marker band in an erroneously extracted image.

FIGS. 16 to 18 show experimental conditions (FIGS. 16 and 17) according to an embodiment of the present disclosure and their results (FIG. 18).

DETAILED DESCRIPTION

Hereinafter, embodiments are described in detail with reference to the accompanying drawings and the contents recited therein, but the scope of the present disclosure is not limited to the embodiments.

The terms used herein have been selected among general terms widely used in the art at the present in consideration of their functions, but they may be changed according to intention of those skilled in the art, customs, appearance of new technologies or the like. In addition, in a specific case, the applicant has selected a term based on his own discretion, and in this case, its meaning will be described herein. Thus, the terms used herein should be interpreted based on their true meanings and the overall disclosure of this specification, without being limited to its simple name.

Figure 1:
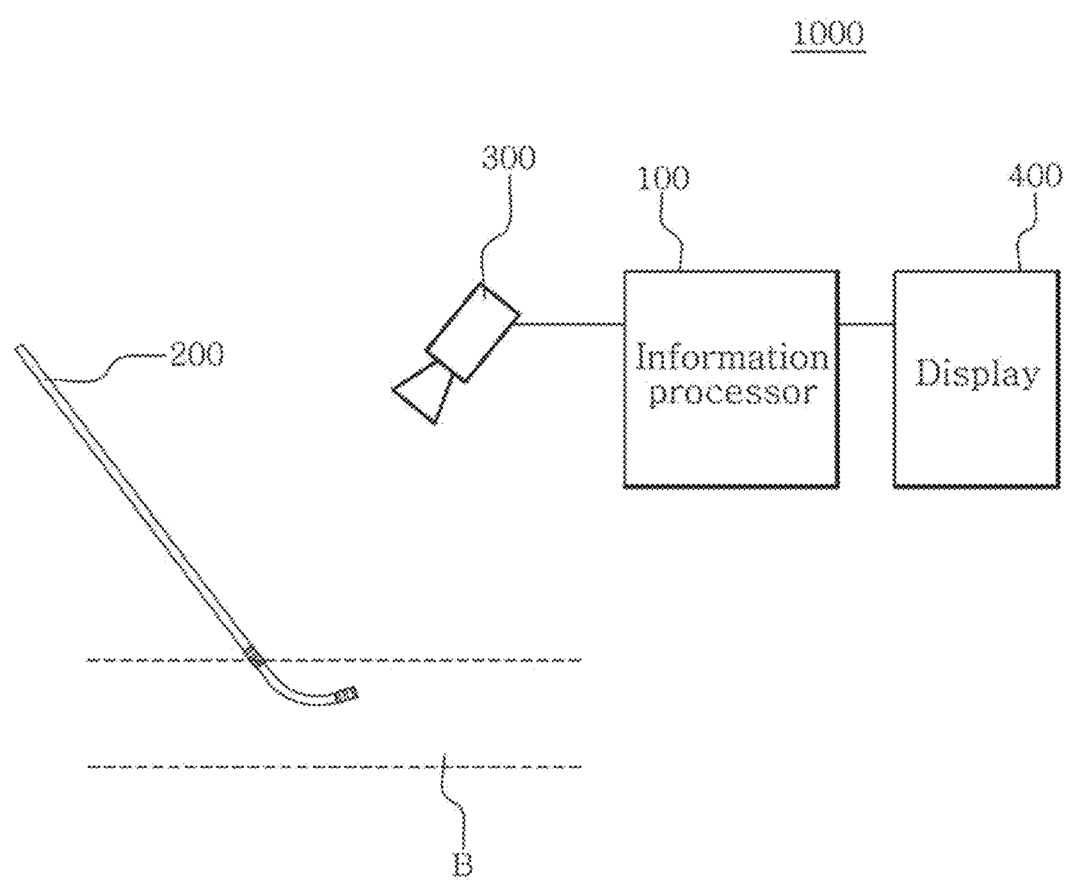
FIG. 1 is a diagram showing an apparatus 1000 for tracking a location of a surgical tool based on a radiographic image according to an embodiment of the present disclosure.

FIG. 1 is a diagram showing an apparatus 1000 for tracking a location of a surgical tool based on a radiographic image according to an embodiment of the present disclosure. Referring to FIG. 1, a photography system 300 photographs a surgical tool 200 which is inserted into a surgical target region (B), and an information processor 100 analyzes the photographed image to estimate a three-dimensional location of the surgical tool 200.

Figure 2A:
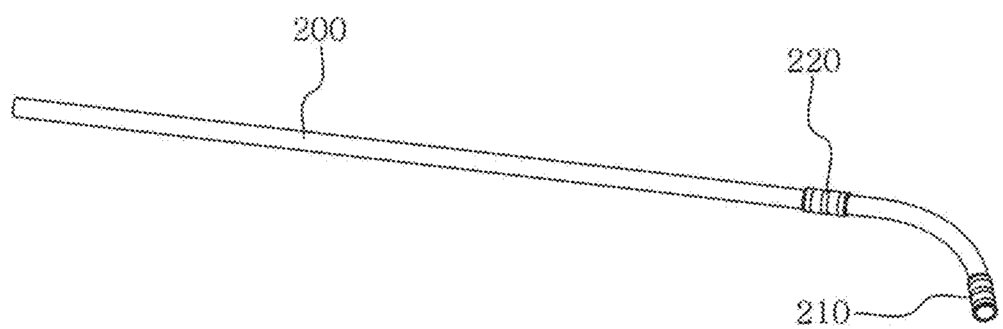
FIGS. 2A and 2B show an example of a surgical tool 200 according to an embodiment of the present disclosure.
Figure 2B:
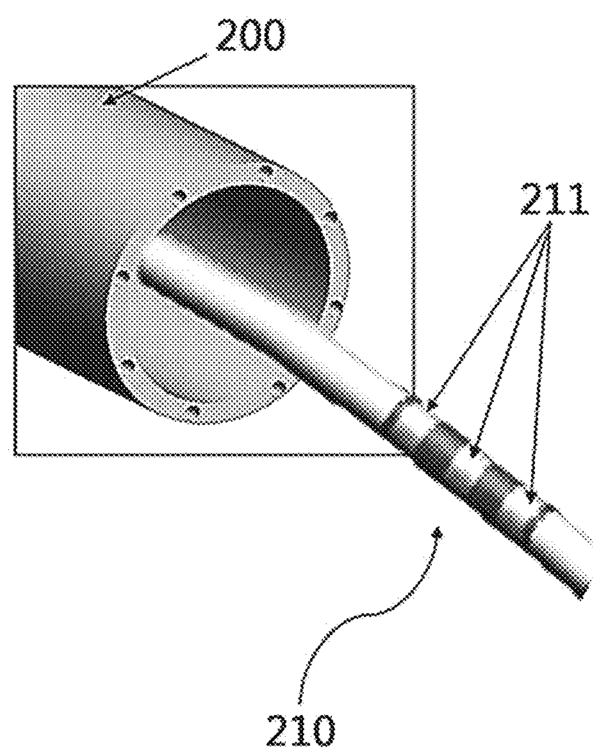
Figure 3:
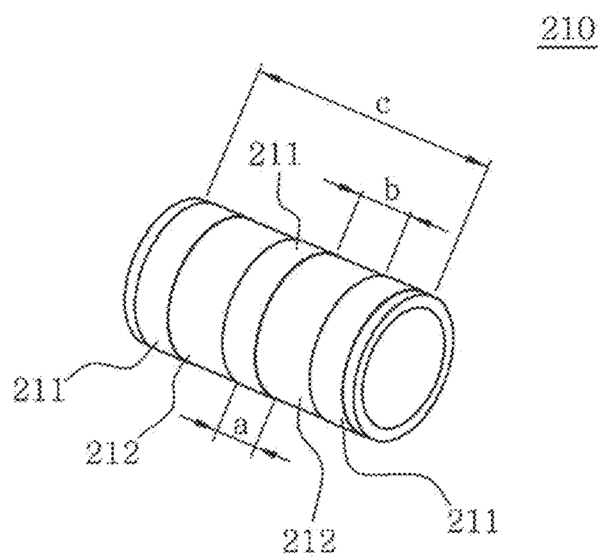
FIG. 3 shows an example of a physical marker frame 210 included in the surgical tool 200.

For this, the apparatus 1000 for tracking a location of a surgical tool based on a radiographic image according to an embodiment may include a photography system 300 configured to photograph a surgical tool having a physical marker frame and an information processor 100 configured to estimate a three-dimensional location of the surgical tool 200 based on the physical marker frame in the photographed image. Here, the physical marker frame may include three or more marker bands which surround a part of the surgical tool 200 or are inserted into the surgical tool. FIGS. 2A and 2B show an example of the surgical tool 200 according to an embodiment of the present disclosure, and FIG. 3 shows an example of a physical marker frame 210 included in the surgical tool 200. In an embodiment, the surgical tool 200 may be made of flexible material which is bendable. However, a portion surrounded by the physical marker frames 210, 220 may be fixed in a linear shape by means of the physical marker frames 210, 220 not to be bent. In other words, even though the surgical tool is made of flexible material, the physical marker frames may be made of rigid materials to surround a part of the surgical tool not to be bent.

In an embodiment, the surgical tool 200 may have a rod shape with a circular section or a polygonal section having a triangular, rectangular or pentagonal shape. In FIG. 2, a cylindrical surgical tool with a circular section is depicted as an example. In addition, the surgical tool 200 may have a circumference which becomes gradually smaller toward an end. In this case, the surgical tool 200 may be inserted more easily. In addition, the surgical tool 200 may be a catheter.

Moreover, the surgical tool 200 may include one or more physical marker frames 210, 220, and at least two physical marker frames 210, 220 may be disposed to have axes oriented in different directions. In other words, as shown in FIG. 2A, one physical marker frame 210 is oriented toward one portion of the bent surgical tool 200, and the other marker frame 220 may be oriented toward another portion of the bent surgical tool 200.

In another embodiment, the physical marker frame may surround an outer surface of the surgical tool 200 as shown in FIG. 2A or be inserted into the surgical tool 200 as a guide wire as shown in FIG. 2B.

Even though FIG. 2A depicts that the physical marker frames 210, 220 are oriented in different directions, in another embodiment, a plurality of physical marker frames 210, 220 may be oriented in the same direction. For example, if the surgical tool 200 has a great length or the three-dimensional location of the surgical tool is demanded more accurately, an additional physical marker frame may be provided.

Even though FIG. 3 shows an example of the physical marker frame 210, other physical marker frames included in the surgical tool 200 may also be configured in the same way. Referring to FIG. 3, the physical marker frame 210 may be composed of three or more marker bands 211 which surround a part of the surgical tool 200. The marker band 211 serves as an identifier for estimating a location of the surgical tool 200 in the photographed image. Meanwhile, since the physical marker frame is made of rigid material, center point of the marker bands may be located on a straight line.

In an embodiment, an interval (b) between the marker bands 211 may be greater than 1.5 times of a width (a) of each marker band, without being limited thereto. In addition, a length (c) of the physical marker frame 210 may be in the range of several mm to several ten mm. The width (a) of the marker band, the interval (b) between the marker bands and the length (c) of the physical marker frame are just examples and may be suitably selected as necessary.

In addition, the marker band 211 may be made of a conductor, for example gold and copper. A region 212 between the marker bands 211 may be made of a non-conductor, for example aluminum, without being limited thereto.

Figure 4:
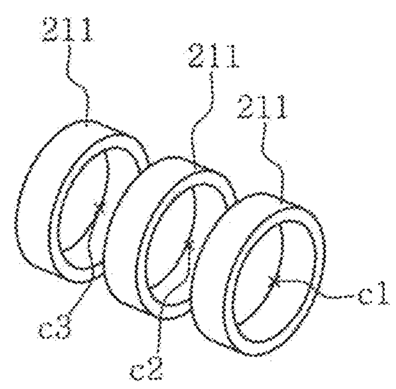
FIG. 4 is a diagram for illustrating an interval (b) between marker bands according to an embodiment of the present disclosure.

FIG. 4 is a diagram for illustrating an interval (b) between marker bands according to an embodiment of the present disclosure. In FIG. 3, the interval (b) represents a distance measured on the outer surface of the physical marker frame. However, in another embodiment, the interval (b) may represent a distance between center points C1 to C3 between the marker bands 211. If the surgical tool 200 has an irregular circumference, in order to define the distance between the marker bands 211, a center point of each marker band may be used as in FIG. 4. In other words, referring to FIG. 4, a distance between C1 and C2 and a distance between C2 and C3 may be defined as the interval (b) between the marker bands.

In an embodiment of the present disclosure, the photography system 300 may be a radiography system, preferably an X-ray photography system. The photography system 300 may photograph the surgical tool 200 inserted into a surgical site B and transfer the photographed image to the information processor 100.

Figure 5:
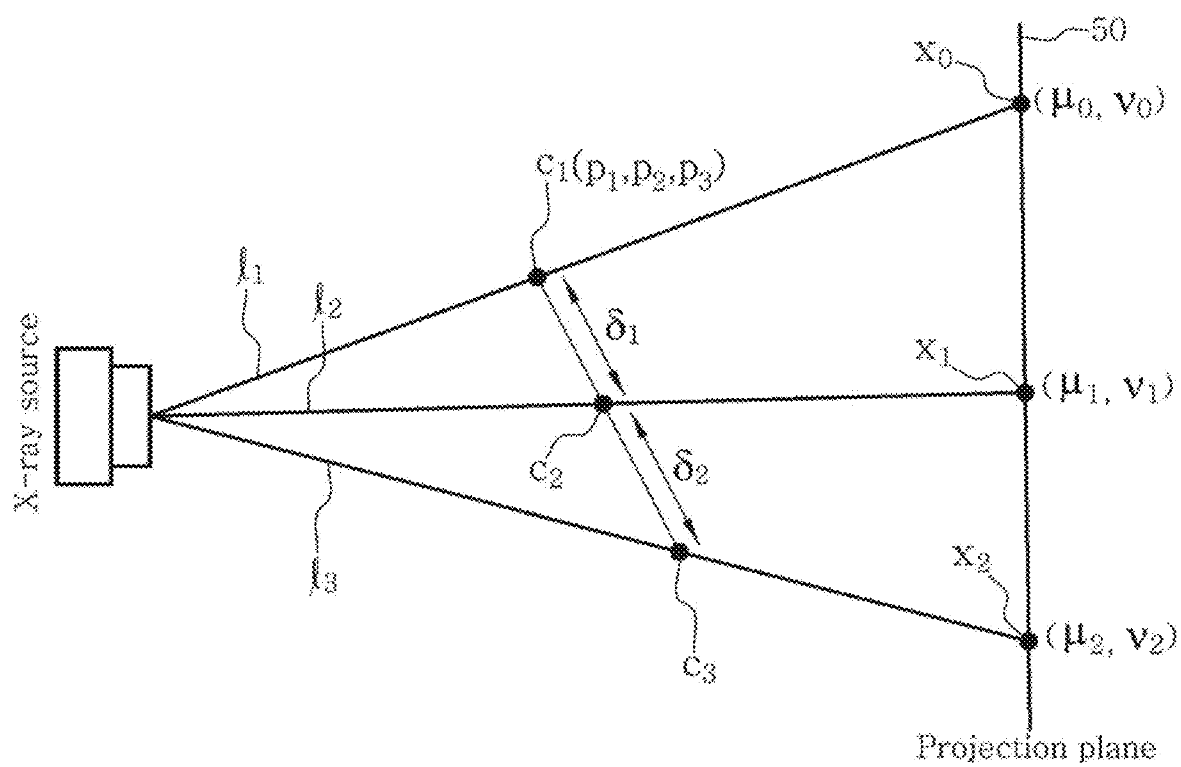
FIG. 5 is a diagram for illustrating a method for calculating a three-dimensional location of a marker band (namely, a three-dimensional location of a surgical tool) according to an embodiment of the present disclosure.

FIG. 5 is a diagram for illustrating a method for calculating a three-dimensional location of a marker band (namely, a three-dimensional location of a surgical tool) according to an embodiment of the present disclosure. In FIG. 5, a true center point $C_1$-$C_3$ of each marker band is exhibited on a projective plane 50 (namely, a detector) by means of an x-ray source (namely, a photography system) as a two-dimensional coordinate $x_0$-$x_2$. Since the photographed image 50 is a two-dimensional plane, additional information is required to estimate a three-dimensional location of the marker band therefrom. Here, the additional information may include a distance between center points of the true marker bands and/or a focus distance of the photography system.

In an embodiment, the information processor 100 may estimate a three-dimensional location of the surgical tool 200 based on the physical marker frame in the photographed image. For example, the information processor 100 may detect a center point $x_0$-$x_2$ in the image with respect to the marker band 211 in the physical marker frame, and estimate a three-dimensional location of the surgical tool based on a distance between the detected center point $x_0$-$x_2$ in the image and the center point $C_1$-$C_3$ of each true marker band and a focus distance f of the photography system 300 (a distance from a photography system source (e.g., an X-ray source) to the detector). As a premise for this, it may be demanded that the marker bands are on the same line in the mark frame, and a distance between the marker bands is already known.

Referring to FIG. 5, the information processor 100 may calculate a three-dimensional location of the marker band after a center point $x_0$-$x_2$ of each marker is detected on the projective plane 50, for the surgical tool including the marker band.

In detail, referring to FIG. 5, the information processor 100 may use coordinates $p_1$, $p_2$, $p_3$ of a marker band $C_1$ serving as a reference among the marker bands in the physical marker frame, distances δ1, δ2 between the markers and a direction vector b to express the other marker bands $C_n$ as in Equation 1 below. Referring to FIG. 5, n is 1 and 2 here.

$$C_n = C_1 + \delta_n b \quad \text{[Equation 1]}$$

In an embodiment, since three true marker bands are on a straight line, the information processor 100 may define a two-dimensional image coordinate $u_n$,$v_n$ of each marker displayed at the projective plane 50 as in Equation 2 below by using a previously measured distance $\delta_1$, $\delta_2$ between marker bands (here, each distance may be a distance between center points of the true marker bands) and a focus distance.

$$u_n = f\frac{p_1 + \delta_n b_1}{p_3 + \delta_n b_3},\quad v_n = f\frac{p_2 + \delta_n b_2}{p_3 + \delta_n b_3},\ n = 0, \ldots, N-1 \qquad \text{[Equation 2]}$$

Here, f represents a focus distance of the photography system (for example, in case of an X-ray photography system, a distance from the X-ray source to the detector).

Equation 2 may be expressed as in Equation 3 below by using three-dimensional location vectors $p_1$, $p_2$, $p_3$ and direction vectors $b_1$, $b_2$, $b_3$.

$$\underbrace{\begin{pmatrix} \delta_0 f & 0 & -\delta_0 u_0 \\ & \vdots & \\ \delta_{N-1} f & 0 & -\delta_{N-1} u_{N-1} \\ 0 & \delta_0 f & -\delta_0 v_0 \\ & \vdots & \\ 0 & \delta_{N-1} f & -\delta_{N-1} v_{N-1} \end{pmatrix}}_{A} \begin{pmatrix} b_1 \\ b_2 \\ b_3 \end{pmatrix} + \underbrace{\begin{pmatrix} f & 0 & -u_0 \\ & \vdots & \\ f & 0 & -u_{N-1} \\ 0 & f & -v_0 \\ & \vdots & \\ 0 & f & -v_{N-1} \end{pmatrix}}_{B} \begin{pmatrix} p_1 \\ p_2 \\ p_3 \end{pmatrix} = \begin{pmatrix} 0 \\ \vdots \\ 0 \end{pmatrix} \qquad \text{[Equation 3]}$$

$$Ab + Bp = 0$$

Equation 3 may be expressed as in Equation 4 below to find an optimizing condition. In addition, the information processor 100 may perform singular value decomposition to solve Equation 4. As a result, the information processor 100 may obtain a symmetric matrix E as in Equation 5 below. Here, an eigenvector corresponding to a minimum eigenvalue of the obtained E may represent a relative direction vector b.

After that, the information processor 100 may calculate a three-dimensional location vector p by means of the optimized eigenvector b and Equation 6 below.

$$\min\|Ab+Bp\| \text{ subject to } b^T b=1 \qquad \text{[Equation 4]}$$

$$E=A^T(I-B(B^T B)^{-1}B^T)A \qquad \text{[Equation 5]}$$

$$p=-(B^T B)^{-1}B^T Ab \qquad \text{[Equation 6]}$$

Through the above process, the information processor 100 may estimate a three-dimensional location of a marker band from the two-dimensional projection image 50 and estimate a three-dimensional location of a surgical tool therefrom. In addition to the above method, the information processor 100 may use various methods in order to estimate three-dimensional locations of true points by using a plurality of points in a two-dimensional image and distances among the true points.

Figure 6:
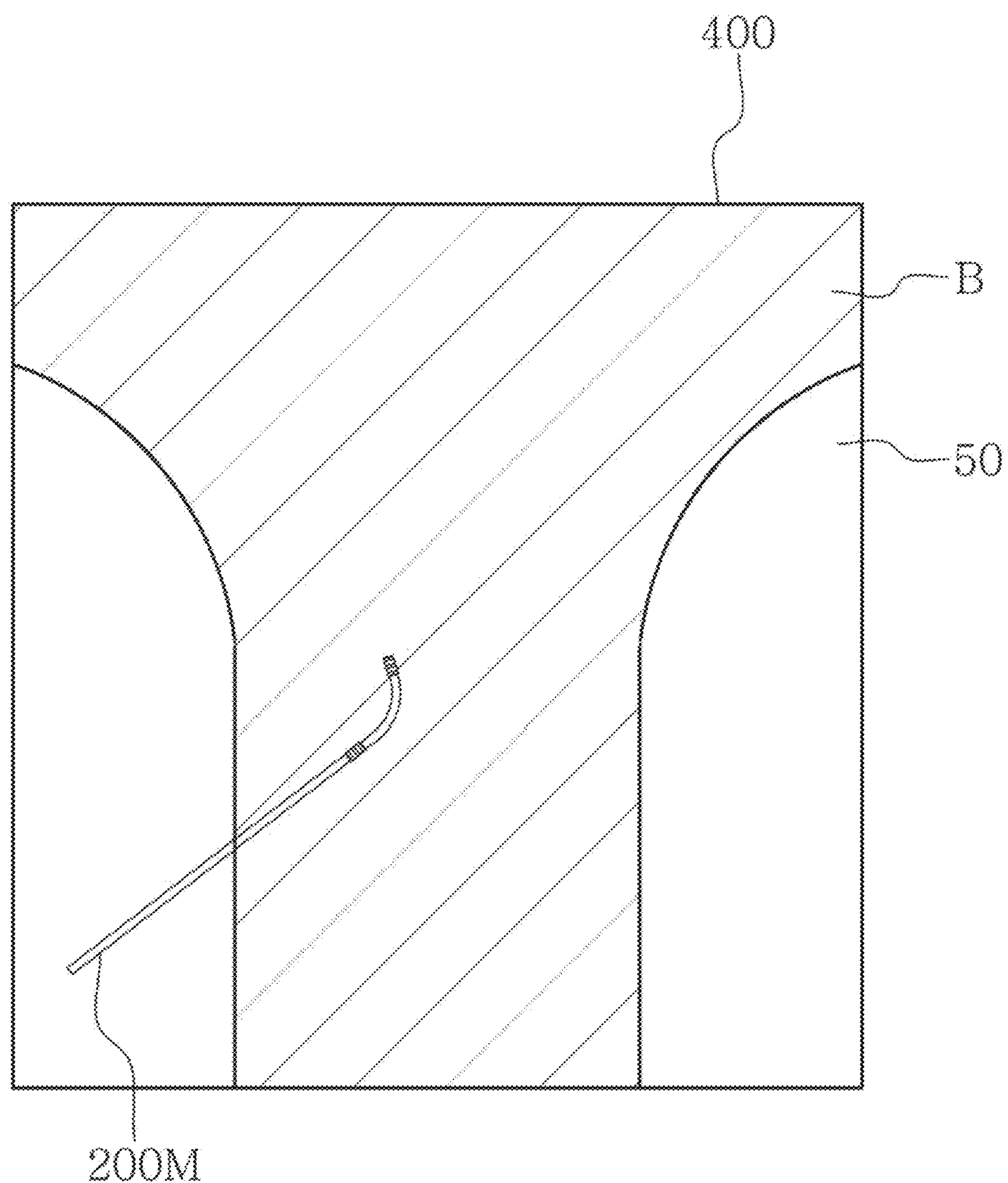
FIG. 6 shows that an image including a surgical tool model 200M is displayed according to an embodiment of the present disclosure.

FIG. 6 shows that an image including a surgical tool model 200M is displayed according to an embodiment of the present disclosure. Referring to FIG. 6, in an embodiment of the present disclosure, the information processor 100 may generate a surgical tool model 200M based on the estimated three-dimensional location of the surgical tool and display the generated surgical tool model 200M on a display 400 together with the image B. Through the image on the display depicted in FIG. 6, a user may figure out a current location of the surgical tool.

Embodiment—A Way to Find a Center Point of a Marker Band More Accurately

Meanwhile, in the method for estimating a three-dimensional location of a marker band as described above, the estimated three-dimensional location may be accurate when a location of a "photographed center point of the marker band in the projection image" (namely, locations x0-x2 in FIG. 5) is accurately calculated. If accurate center points of marker bands are not extracted at a two-dimensional projection image, an erroneous direction vector b is calculated, and thus a serious error may be generated at a depth value (namely, a Z axis) of the marker band. For example, when a distance between marker bands is very smaller than a focus distance since vary minute marker bands are applied to a minute surgical tool, a greater error may be generated.

Figure 8A:
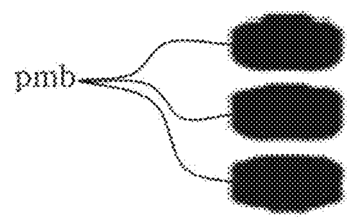
FIGS. 8A to 8C and FIG. 9 show a process of processing a projection image to determine a center point of a marker band according to an embodiment of the present disclosure.

In the present disclosure, the two-dimensional projection image 50 which has photographed the marker band may determine center points of marker bands and then determine three-dimensional locations of the marker bands based on coordinates or intervals of the determined center points. However, since the marker band has a volume, if the marker band is projected to a projection image, the marker band is exhibited to have a predetermined area as shown in FIG. 8A. In addition, depending on an inclination angle of the physical marker frame in the three-dimensional space, area and size of the marker band projected to the projection image are changed. Thus, it is very important to determine a center point of each marker band in the projection image.

Figure 7A:
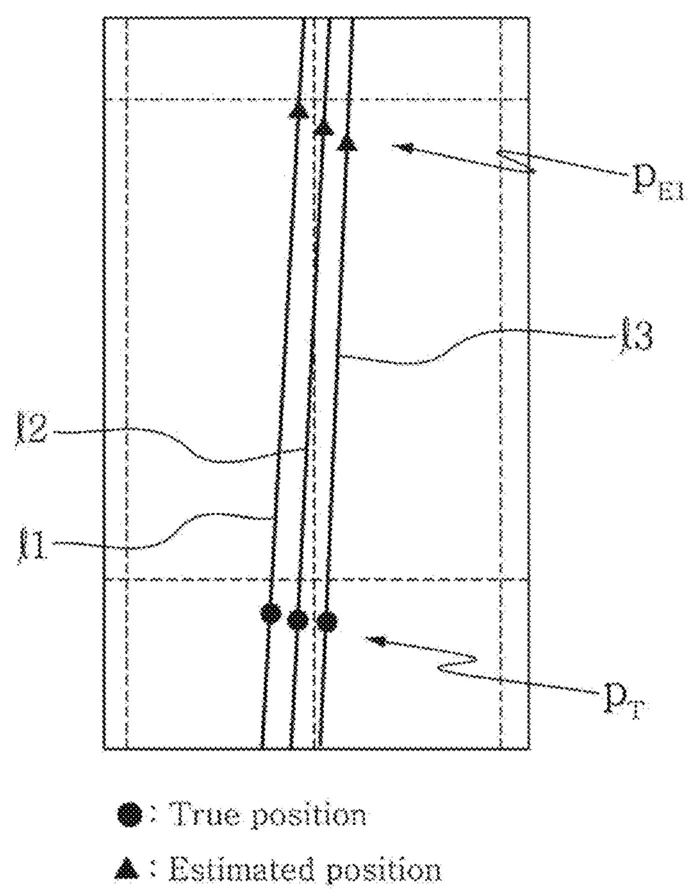
Figure 7B:
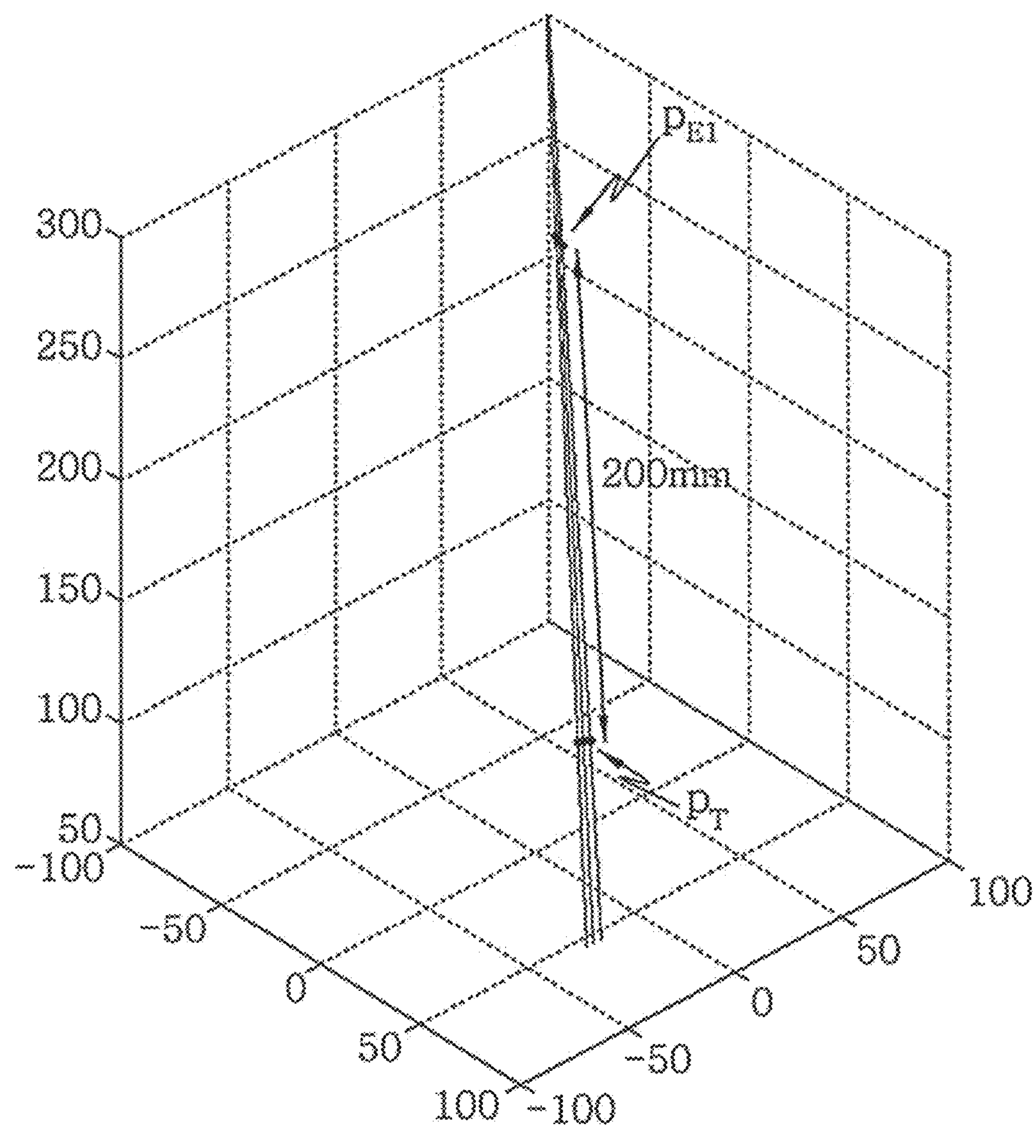

FIGS. 7A to 7C show experimental examples for illustrating a case where an error is generated between a true marker frame and a three-dimensional location of a marker frame estimated based on a center point of the marker band in an erroneously extracted image.

In detail, in FIGS. 7A to 7C, a marker band whose three-dimensional coordinate of a center point is known is generated in a three-dimensional space, and the generated marker band is projected onto a two-dimensional plane to obtain a projection image. A marker band having a predetermined area is projected to and exhibited on the projection image, and a location where the center point of the marker band is projected may also be known. In FIG. 7C, "the true position" represents a location of a center point of a marker band projected in the projection image. Three marker bands are provided, and three two-dimensional coordinates (x,y) are exhibited.

Meanwhile, in FIG. 7C, "Estimated position" represents a center point of a marker band which is calculated from a marker band having a predetermined area in the projection image. As a result of the above experiment, an average error between the estimated position in the projection image and the true position is about 1 pixel. It is found that this error causes an error of about 200 mm in a depth direction (a Z axis) on the three-dimensional space as shown in FIG. 7B.

In detail, in FIGS. 7A and 7B, $p_{E1}$ represents a result (an estimated position) obtained by determining a center point of a marker band according to an existing method (using any algorithm for finding a center point in an area) based on an image to which a virtual marker band generated in a three-dimensional space is projected, and then determining a three-dimensional location according to the method described above with reference to Equations 1 to 6. Also, $p_T$ represents a result (a true position) obtained by determining a three-dimensional location of a marker band based on a location on a two-dimensional plane to which a known center point of a virtual marker band is projected. In other words, $p_{E1}$ is obtained by determining a center point at a 'marker band having a predetermined area' in the projection image and determining a three-dimensional location of the marker band based on the determined location of the center point, and $p_T$ is obtained by projecting a 'known center point of a marker band in a three-dimensional space' onto a two-dimensional plane to determine a projected center point (namely, it is not needed to calculate the center point in the area since the point is projected) and determining a three-dimensional location of the marker band based on the determined location of the center point.

Therefore, in order to reduce the error, it is required to find an accurate center point of the marker band in the two-dimensional projection image.

In an embodiment, the information processor 100 may resample the photographed image and determine a center point of each marker band in the resampled image. According to an embodiment of the present disclosure, the information processor 100 may process the projection image as follows in order to determine the center point of the marker band more accurately in the projection image photographed by the photography system 300.

FIGS. 8A to 8C and FIG. 9 show a process of processing a projection image to determine a center point of a marker band according to an embodiment of the present disclosure.

Figure 8B:
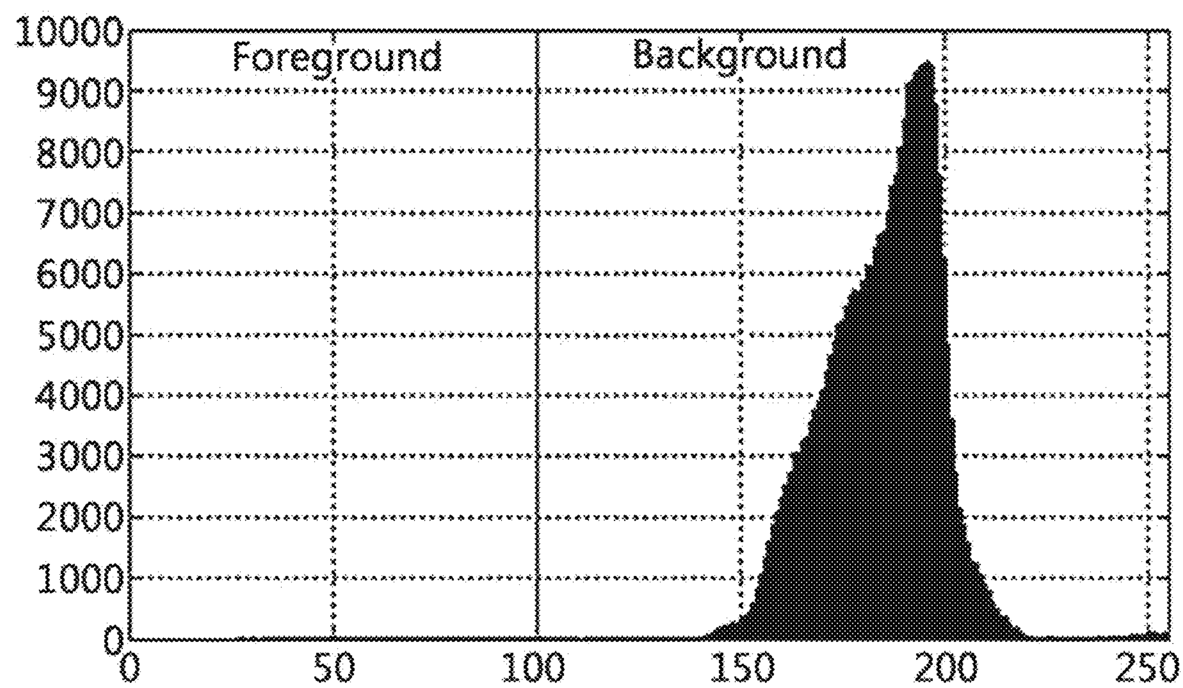
Figure 8C:
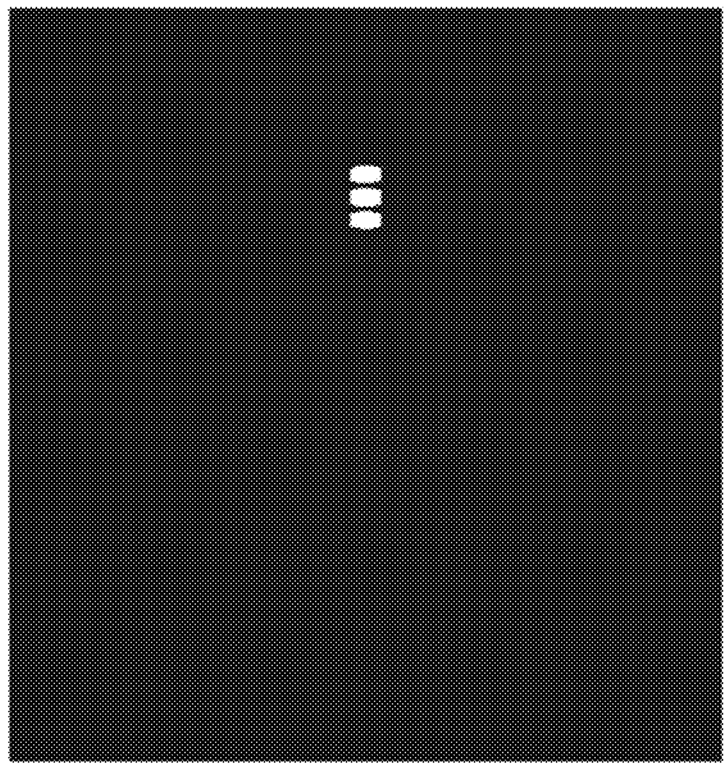

Referring to FIGS. 8A to 8C, the information processor 100 may calculate a specific threshold of a circular projection image (FIG. 8A) obtained by the photography system 300 based on the brightness histogram, separate objects (a projected marker band, a projected marker band (pmb)) from the background in the projection image, and then display the objects as a binary image as shown in FIG. 8C. FIG. 8B shows a single specific threshold calculated for the projection image, and in FIG. 8B, an X axis represents a brightness value, and a Y axis represents the number of pixels. Various existing techniques may be used for the center point of each area of the projected marker band having a predetermined area as described above.

Figure 9:
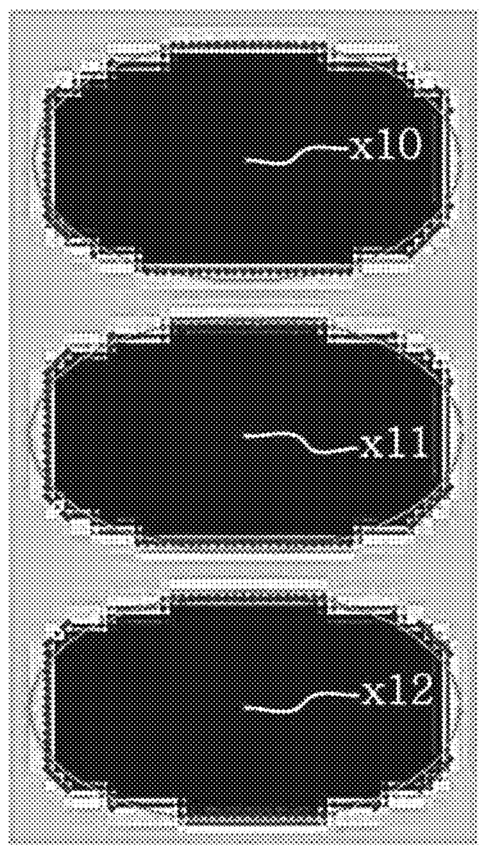

In an embodiment, as shown in FIG. 9, the information processor 100 may resample a specific portion (or, an entire portion) of a two-dimensional image including a marker band to be enlarged and then process the image in order to minimize the change of image quality. After that, the information processor 100 may determine center points x10, x11, x13 of the marker bands in the resampled image. For example, center points of the marker bands in the projection image may be primarily determined by the method described with reference to FIGS. 8A to 8C, and the center points of the marker bands in the projection image may be corrected by means of secondary resampling.

Figure 10:
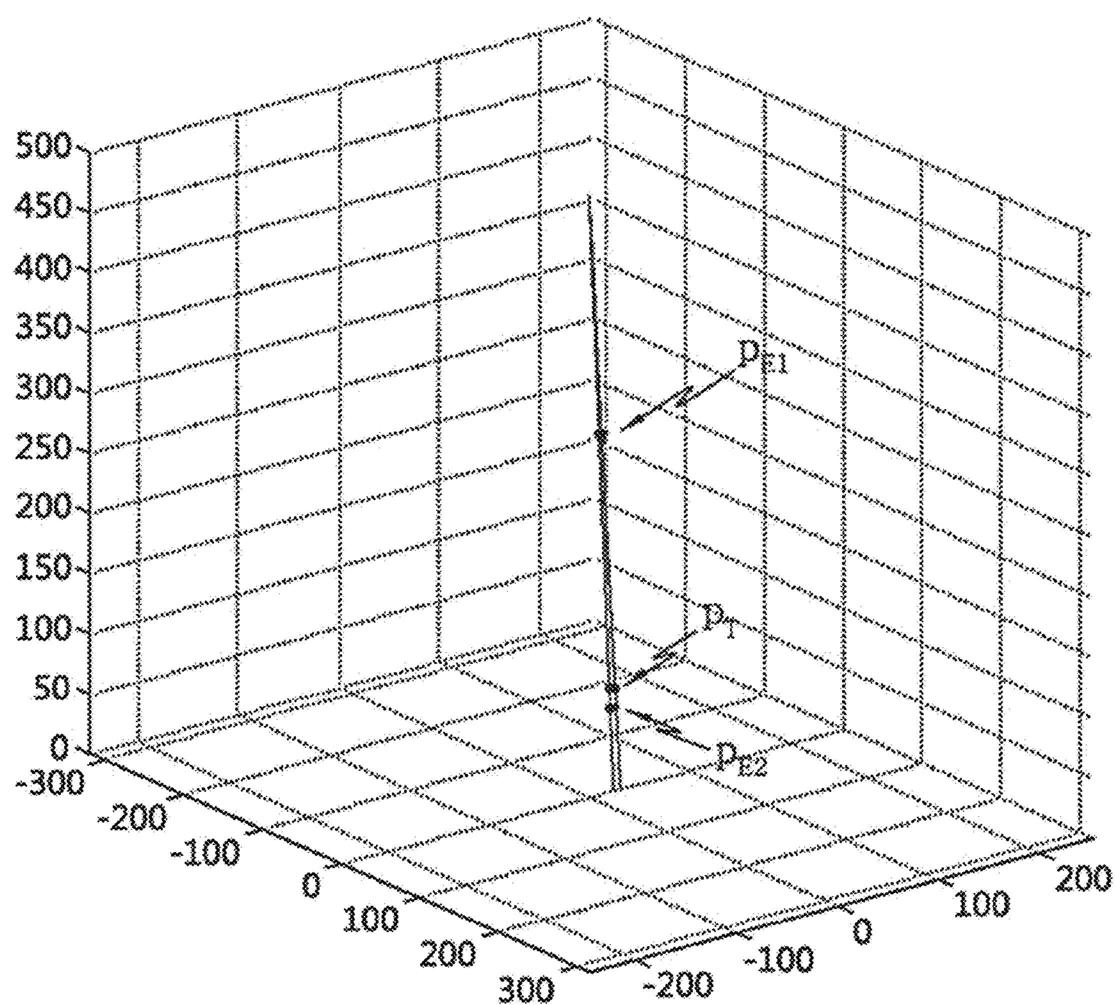
FIG. 10 shows a location $p_T$ of a true marker band and locations $p_{E1}$, $p_{E2}$ of estimated marker bands in a three-dimensional space.

FIG. 10 shows a location $p_T$ of a true marker band and locations $p_{E1}$, $p_{E2}$ of estimated marker bands in a three-dimensional space. In detail, in FIG. 10, the marker band $p_T$ determined based on a true center point of a marker band projected to the two-dimensional projection image, the marker band psi determined based on a center point calculated from an area of a marker band projected to a two-dimensional projection image according to an existing technique, and a marker band $p_{E2}$ determined based on a center point calculated from an area of a marker band projected to a two-dimensional projection image according to the method described with reference to FIGS. 8A to 8C and FIG. 9 are displayed together on a three-dimensional virtual space. Referring to FIG. 10, it may be found that $p_{E2}$ is closer to a location $p_T$ of the true marker band in comparison to psi.

Referring to FIG. 10, according to the method proposed in the present disclosure, the center point of the marker band in the projection image is corrected so that the interval between the true position $p_T$ of the marker band and the estimated position $p_{E2}$ becomes smaller in comparison to the case of psi, but there is still an error. In order to determine a center point of a marker band more accurately, the following method may be additionally or alternatively used.

In an embodiment, the information processor 100 may generate a virtual marker frame corresponding to the physical marker frame on a three-dimensional virtual space, project the generated virtual marker frame to the photographed projection image, adjust a location of the virtual marker frame on the three-dimensional space so that the virtual marker frame projected to the projection image is matched with the physical marker frame, and then, when the projected virtual marker frame and the projected physical marker frame are matched in the frame image, determine the center point of the marker band of the virtual marker frame in the image as a center point of the marker band of the physical marker frame.

Also, in an embodiment, the information processor 100 may adjust a location of the virtual marker frame along a line (I1-I3 in FIG. 5 or 7A) connecting the photography system and the physical marker frame, on the three-dimensional virtual space.

In an embodiment, the information processor 100 may generate a virtual marker frame (vmp) and determine (or, correct) a center point of the marker band in the projection image based on the generated virtual marker frame and the image to which the true marker band is projected.

Figure 11:
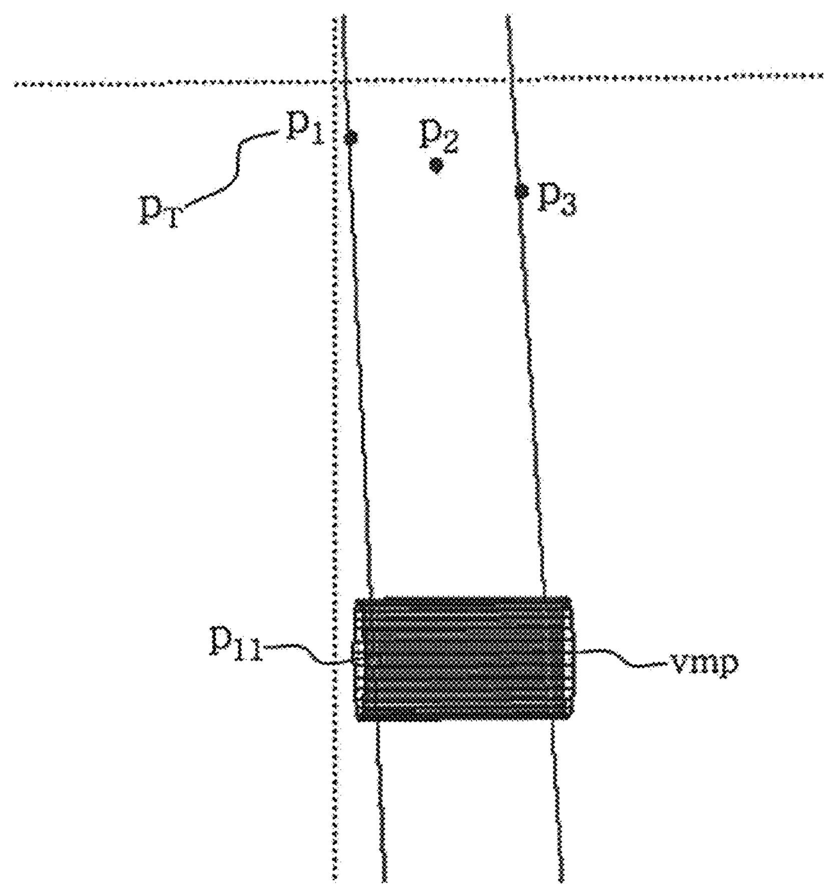
FIG. 11 shows a true marker band and a virtual marker frame existing at the location $p_{E2}$ of the marker band of FIG. 10.

FIG. 11 shows a true marker band and a virtual marker frame existing at the location $p_{E2}$ of the marker band of FIG. 10. In an embodiment, the virtual marker frame may be set 1) to have a posture parallel to the XY axis on the three-dimensional virtual space, 2) to have the same size as the true physical marker frame, and 3) to correspond to the center point of the marker band in the virtual marker frame and a center point (p11 in FIG. 11) of at least one marker band among the true marker bands.

Figure 12:
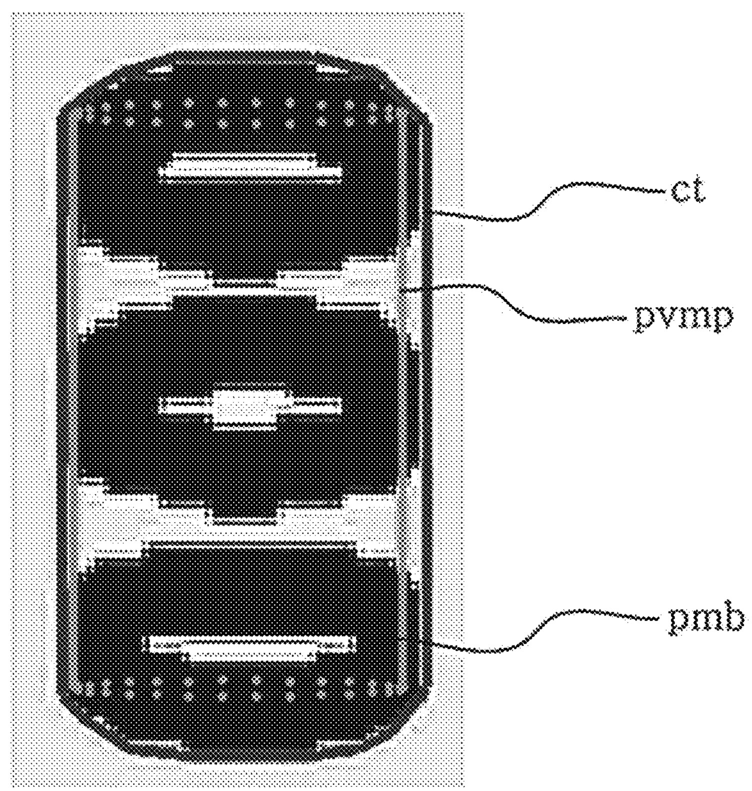
FIG. 12 shows a projection image of FIG. 11.

FIG. 12 shows a projection image of FIG. 11. Referring to FIG. 12, the projected physical marker frame is not matched with a contour of the projected marker band but is included therein.

In an embodiment, the information processor 100 may adjust a location of the virtual marker frame on the three-dimensional space so that the virtual marker frame (vpm) projected in the projection image is matched with the projected marker band. If the virtual marker frame (vpm) projected in the projection image is matched with the projected marker band, locations of the virtual marker frame and the true marker band will also correspond to each other on the three-dimensional space.

Therefore, when the virtual marker frame (vpm) projected in the projection image is matched with the projected marker band, the information processor 100 may determine a location of the virtual marker frame as a location of the true marker band.

In order to perform the above calculation efficiently, the information processor 100 may compare a contour (ct) of the projected marker band with the projected virtual marker frame and determine whether they are matched.

The information processor 100 may match the virtual marker frame (vpm) projected in the projection image and the projected marker band by using the following method.

Figure 13:
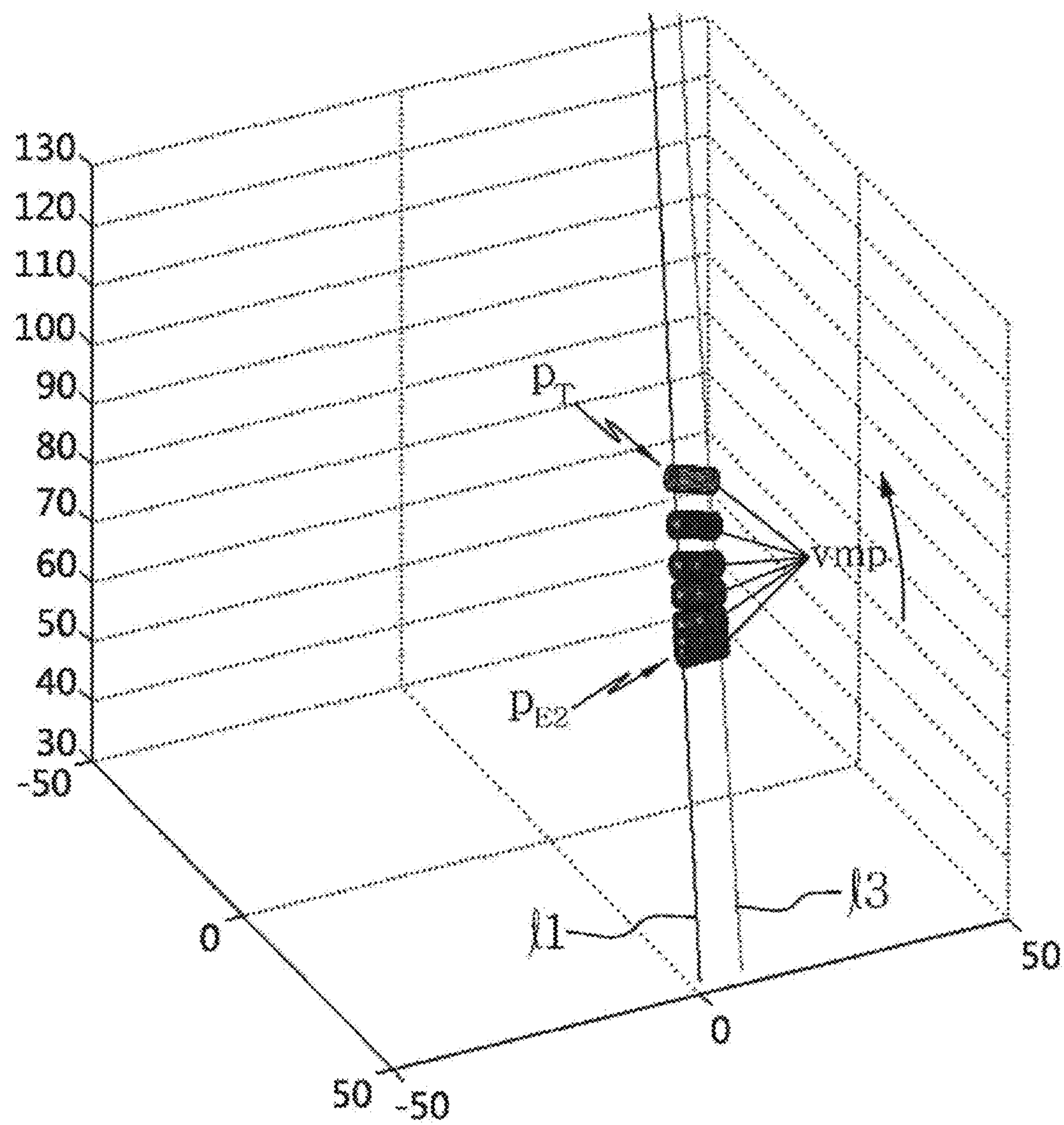
FIG. 13 shows a location-adjustable virtual marker frame and a location $p_T$ of a true marker band.
Figure 14:
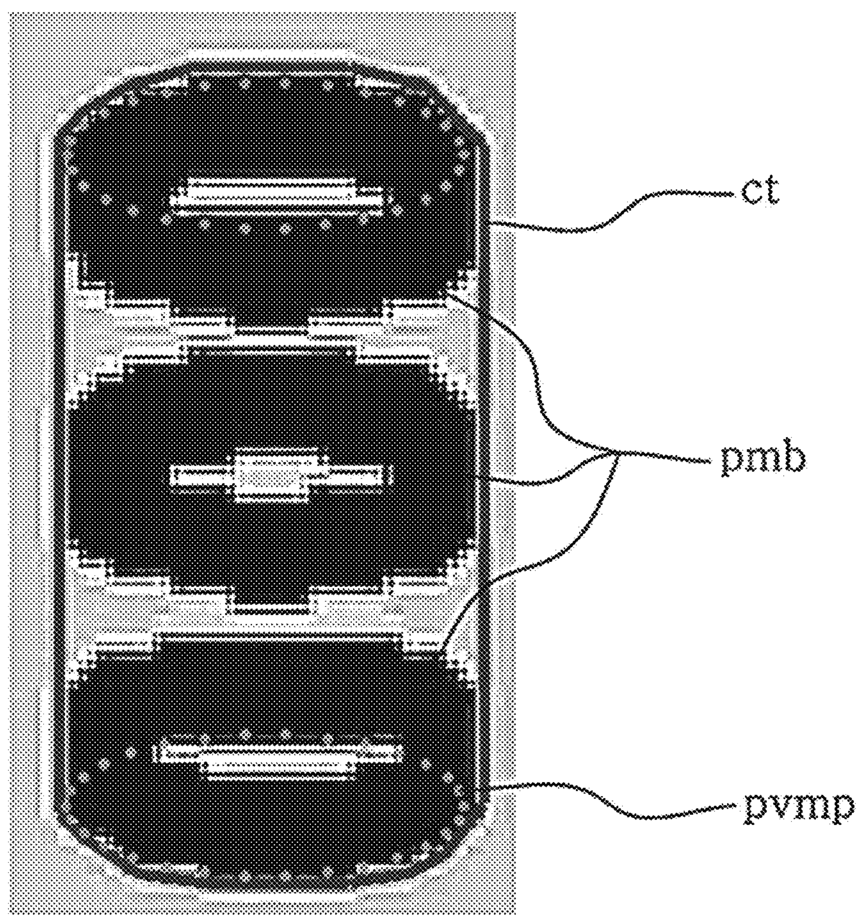
FIG. 14 shows a state where a projected virtual marker frame is matched with a contour of a projected marker band.

FIG. 13 shows a location-adjustable virtual marker frame and a location $p_T$ of a true marker band, and FIG. 14 shows a state where a projected virtual marker frame is matched with a contour of a projected marker band.

Referring to FIG. 13, the information processor 100 may move the virtual marker frame to compare the projected virtual mark frame with a contour of the projected marker band. For example, if the projected virtual mark frame exists in the contour of the projected marker band, the projected virtual mark frame may be moved along a +Z axis or in an opposite direction. Here, the unit of movement may be suitably adjusted.

The information processor 100 may move the virtual marker frame along at least one of lines I1-I3 between the center point of each marker band and the photography system 300. As shown in FIG. 13, the information processor 100 may move the virtual marker frame little by little along a +Z axis and determine whether the virtual marker frame is matched in the projection image.

Figure 15:
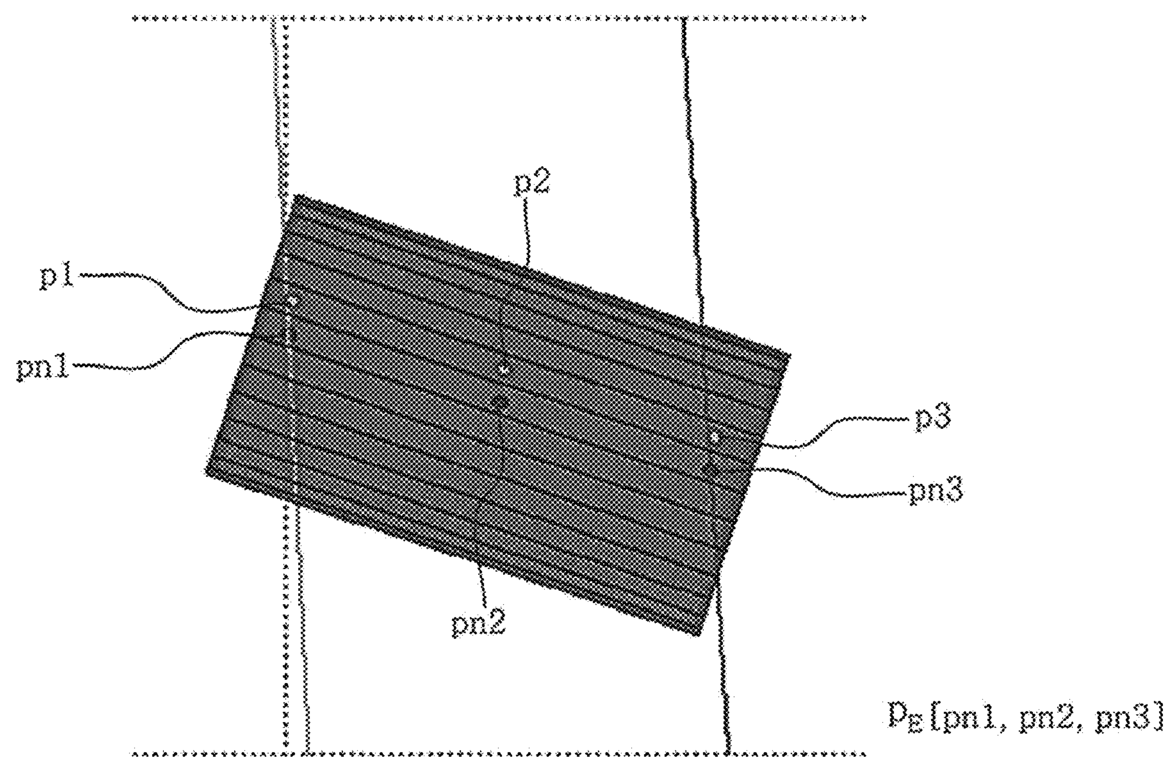
FIG. 15 shows a virtual marker frame finally moved after its matching process is completed, center points pn1, pn2, pn3 of marker bands included in the virtual marker frame, and center points $p_{T1}$, $p_{T2}$, $p_{T3}$ of true marker bands.

FIG. 15 shows a virtual marker frame finally moved after its matching process is completed, center points pn1, pn2, pn3 of marker bands included in the virtual marker frame, and center points $p_{T1}$, $p_{T2}$, $p_{T3}$ of true marker bands. Referring to FIG. 15, it may be found that the center point of the marker band of the virtual marker frame is located very close to the center point of the true marker band. Hereinafter, experiment results using the above matching process will be described.

Meanwhile, for convenience, it has been described that a virtual marker frame is generated and projected to a projection image to be matched with a marker band in the projection image. However, in another embodiment, it is also possible to adjust a location of the virtual marker band so that a virtual marker band is generated and projected to a projection image to be matched with a marker band in the projection image.

Figure 16:
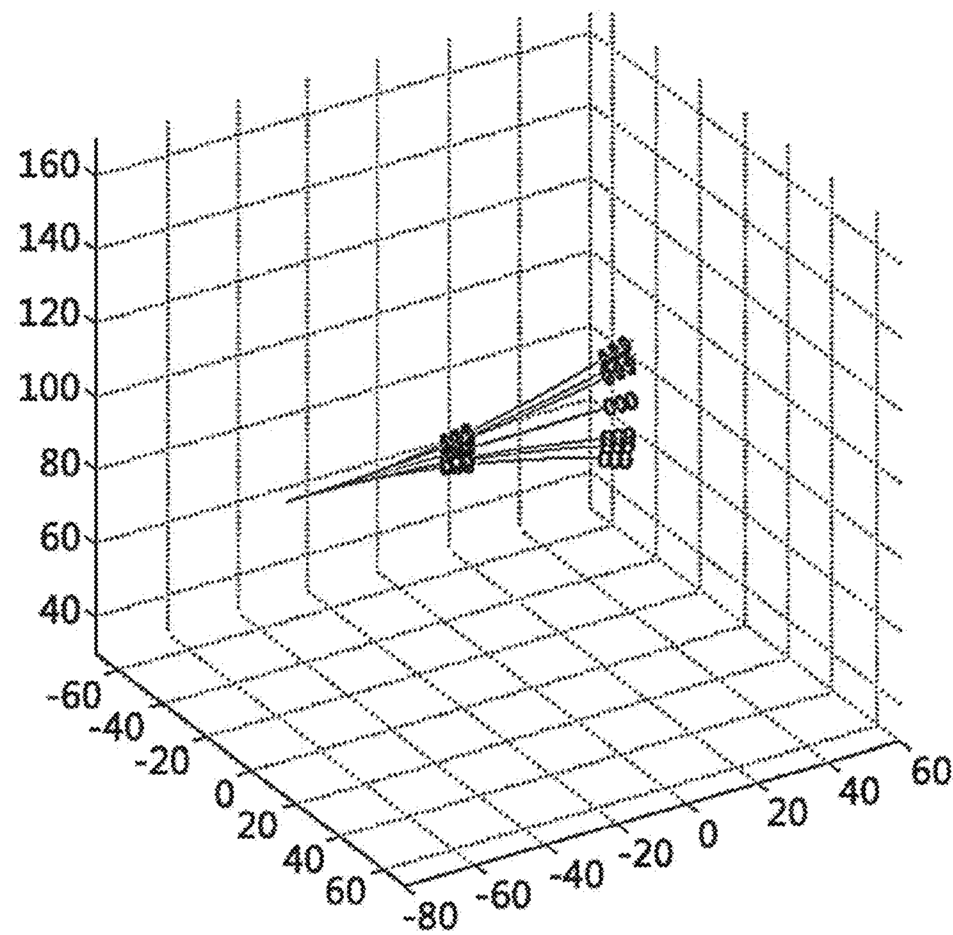
Figure 16:
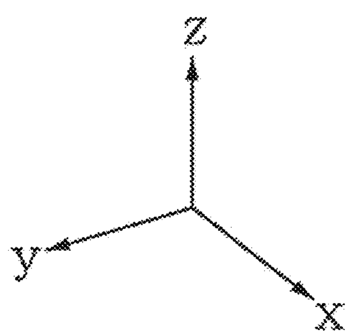
Figure 17:
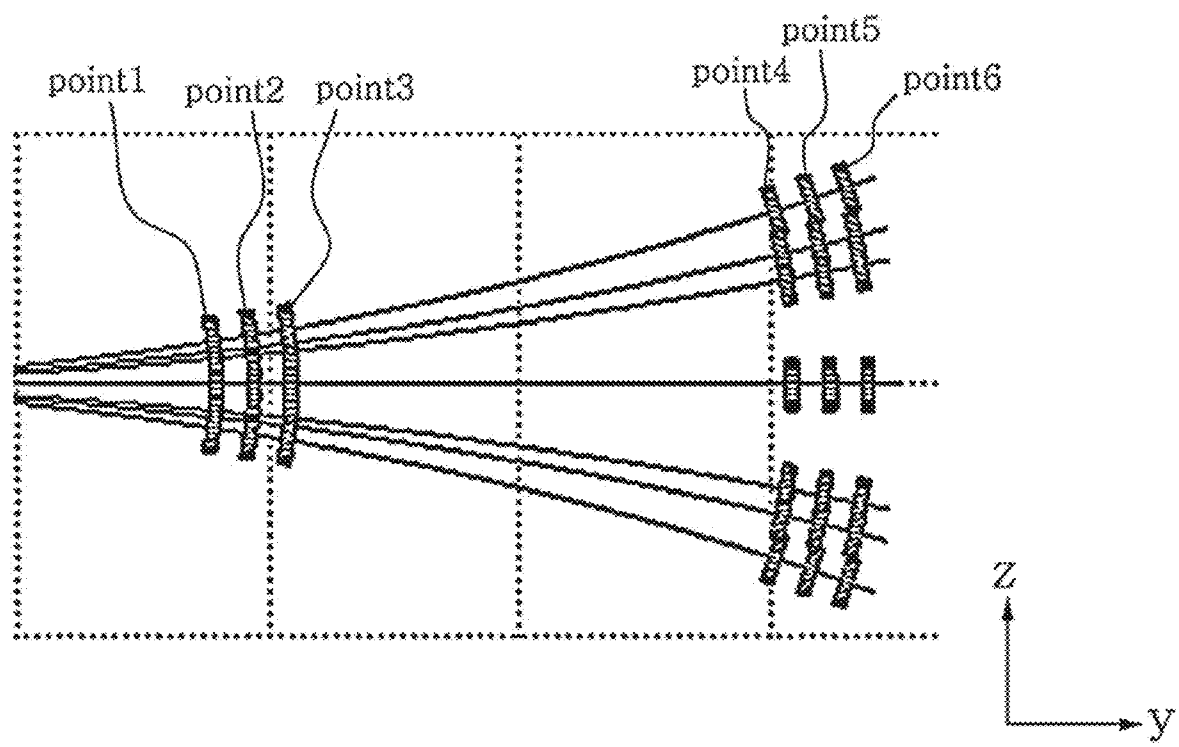

FIGS. 16 to 18 show experimental conditions and their results according to an embodiment of the present disclosure. In order to verity the experiment results of the present disclosure, seven marker bands having different curvature radii are generated under a virtual three-dimensional environment (see FIG. 16), and a virtual projection image is generated based on them. The generated image is used to extract a three-dimensional location by means of the method proposed in the present disclosure, which results in an average distance error of 0.694 mm, a minimum distance error of 0.095 mm, and a maximum distance error of 2.034 mm. This result has a value smaller than 4 mm which is a thickness of the marker band generated for the verification, and the estimated three-dimensional location of the marker band is included in the marker band.

The method for tracking a location of a surgical tool based on an image according to an embodiment of the present disclosure may be implemented using the components of the apparatus 1000 for tracking a location of a surgical tool based on an image as described above. In an example, the method for tracking a location of a surgical tool based on an image may include: by a photography system, photographing a surgical tool having a physical marker frame composed of three or more marker bands; by an information processor, detecting a center point of each marker band in the photographed image; and by the information processor, estimating a three-dimensional location of the surgical tool based on a distance between the detected center point and a center point of an actual marker band.

The above method may be implemented as an application or program commands executable by various kinds of computer means and recorded on a computer-readable recording medium. The computer-readable recording medium may include program commands, data files, data structures or the like solely or in combination. The program commands recorded on the medium may be specially designed or configured for the present disclosure or known to and available by computer software engineers.

The computer-readable recording medium includes, for example, magnetic media such as a hard disk, a floppy disk and a magnetic tape, optical media such as CD-ROM and DVD, magneto-optical media such as a floptical disk, hardware devices such as ROM, RAM and a flash memory, specially configured to store and perform program commands, or the like. The program commands include not only machine codes made by a complier but also high-level language codes executable by a computer by using an interpreter. The hardware device may be configured to operate as at least one software module to perform the operations of the present disclosure, or vice versa.

In addition, even though the embodiments have been illustrated and explained, the present disclosure is not limited to the specific embodiments as described above but can be modified in various ways without departing from the scope of the claims by those having ordinary skill in the art, and such modifications must not be separately understood from the features of the present disclosure.

In addition, in the specification, both an article invention and a process invention have been described, and the explanations of both inventions may be supplementary to each other.

What is claimed is:

1. An apparatus for tracking a location of a surgical tool based on radiography, comprising:
   - a photography system configured to create a photographic image of the surgical tool having two or more physical marker frames; and
   - an information processor configured to estimate the location of the surgical tool based on the two or more physical marker frames in the photographic image, wherein the location is a three-dimensional location,
   - wherein each physical marker frame includes three or more marker bands which surround a part of the surgical tool,
   - wherein the information processor is configured to detect a center point of each marker band in the photographic image, and
   - wherein
   - the information processor is further configured to estimate the three-dimensional location of the surgical tool, after insertion of the surgical tool into a surgical site, based on a distance between the detected center point in the photographic image and a corresponding center point of a true marker band,
   - each of the two or more physical marker frames is made of rigid material and the surgical tool is made of flexible material which is bendable,
   - the part of the surgical tool is fixed in a linear shape by being surrounded by the two or more physical marker frames,
   - the two or more physical marker frames have axes different from each other, and the information processor is further configured to:

generate a virtual marker frame corresponding to at least one of the physical marker frames in a three-dimensional virtual space, project the generated virtual marker frame onto the photographic image, adjust a location of the virtual marker frame in the three-dimensional virtual space so that the virtual marker frame projected onto the photographic image is matched with the at least one physical marker frame, and when the projected virtual marker frame is matched with the at least one physical marker frame, the information processor is configured to determine a center point of a marker band of the virtual marker frame in the photographic image as a corrected center point of a corresponding marker band of the at least one physical marker frame.

2. The apparatus according to claim 1, wherein an interval between the marker bands is greater than 1.5 times of a width of each marker band.

3. The apparatus according to claim 1, wherein the photography system is a radiography system, and wherein the marker bands are made of a conductive material, and material different from the material of the marker bands is provided between the marker bands.

4. The apparatus according to claim 3, wherein the radiography system is an X-ray photography system.

5. The apparatus according to claim 3, wherein the surgical tool is a bendable catheter.

6. The apparatus according to claim 1, wherein the information processor is further configured to generate a surgical tool model corresponding to the surgical tool in the three-dimensional virtual space, based on the estimated three-dimensional location of the surgical tool, and wherein the information processor is configured to display the generated surgical tool model on a display together with the photographic image.

7. The apparatus according to claim 1, wherein the information processor is configured to resample the photographic image and determine a center point of each marker band in the resampled photographic image.

8. The apparatus according to claim 1, wherein the information processor is further configured to adjust the location of the virtual marker frame based on a plurality of lines projected from the photography system that pass respectively through each of respective true center points of the three or more marker bands of at least one of the physical marker frames and through respective corresponding two-dimensional coordinates on a projection plane of the photography system.

9. A method for tracking a location of a surgical tool based on radiography, comprising:

by a photography system, creating a photographic image of the surgical tool, the surgical tool having two or more physical marker frames each composed of three or more marker bands;

by an information processor, detecting a center point of each marker band in the photographic image; and by the information processor, estimating the location of the surgical tool, after insertion of the surgical tool into a surgical site, based on a distance between the detected center point and a corresponding center point of a true marker band, wherein the location is a three-dimensional location;

wherein the detected center point is in a projection plane generated by the photography system, each of the two or more physical marker frames is made of rigid material and the surgical tool is made of flexible material which is bendable, a part of the surgical tool is fixed in a linear shape by being surrounded by the two or more physical marker frames, and the two or more physical marker frames have axes different from each other, the method further comprising, by the information processor:

generating a virtual marker frame corresponding to at least one of the physical marker frames in a three-dimensional virtual space, projecting the generated virtual marker frame onto the photographic image, adjusting a location of the virtual marker frame in the three-dimensional space so that the virtual marker frame projected onto the photographic image is matched with the at least one physical marker frame, and when the projected virtual marker frame is matched with the at least one physical marker frame, determining a corrected center point of a marker band of the virtual marker frame in the photographic image as a center point of a corresponding marker band of the at least one physical marker frame.

10. The apparatus according to claim 1, wherein the information processor is further configured to determine the distance between the detected center point in the photographic image and the corresponding center point of the true marker band based at least partly on a focus distance of the photography system.

11. The apparatus according to claim 10, wherein the information processor is further configured to estimate the three-dimensional location of the surgical tool based on three-dimensional coordinates of a reference marker band of the three or more marker bands, distances between the reference marker band and others of the three or more marker bands, and a direction vector.

12. The apparatus according to claim 1, wherein the information processor is further configured to:

resample a specific portion of a two-dimensional image including at least one of the three or more marker bands;

process an enlarged image corresponding to the resampled specific portion to minimize a change in image quality; and determine the corresponding center point of the true marker band by calculating a specific threshold of a circular projection image obtained based on a brightness histogram, and separating a projected marker band depicting the at least one of the three or more marker bands from a background in the projection image.

* * * * *